(12) United States Patent
Stuke et al.

(10) Patent No.: US 9,341,546 B2
(45) Date of Patent: May 17, 2016

(54) APPARATUS FOR MATERIALS TESTING OF TEST OBJECTS USING X-RAYS

(75) Inventors: Ingo Stuke, Reinfeld (DE); Til Florian Guenzler, Lingen (DE); Michael Wuestenbecker, Lutjensee (DE); Jan Kraemer, Lubeck (DE); Holger Lux, Bargteheide (DE); Nicolas Bretzke, Kirchbarkau (DE)

(73) Assignee: GE SENSING & INSPECTION TECHNOLOGIES GMBH, Hurth (DE)

( * ) Notice: Subject to any disclaimer, the term of this patent is extended or adjusted under 35 U.S.C. 154(b) by 1096 days.

(21) Appl. No.: 13/144,306

(22) PCT Filed: Jan. 13, 2009

(86) PCT No.: PCT/EP2009/000152
§ 371 (c)(1),
(2), (4) Date: Nov. 10, 2011

(87) PCT Pub. No.: WO2010/034361
PCT Pub. Date: Apr. 1, 2010

(65) Prior Publication Data
US 2012/0045033 A1    Feb. 23, 2012

(30) Foreign Application Priority Data
Sep. 24, 2008   (EP) ................................ 2008/008072

(51) Int. Cl.
*G01N 23/04*    (2006.01)
*G01M 17/013*   (2006.01)

(52) U.S. Cl.
CPC ............. *G01M 17/013* (2013.01); *G01N 23/04* (2013.01); *G01N 2223/308* (2013.01);
(Continued)

(58) Field of Classification Search
CPC ... G01V 5/0066; G01V 5/0008; G01V 5/005; G01N 23/04
USPC ............................................................ 378/57
See application file for complete search history.

(56) References Cited

U.S. PATENT DOCUMENTS 3,843,888 A    10/1974  Fox
4,449,226 A *   5/1984  Collmann ........................ 378/58
(Continued)

FOREIGN PATENT DOCUMENTS

DE    2325240 A1    12/1973
DE    2237153 A1     2/1974
(Continued)

OTHER PUBLICATIONS

Schmoldt et al., "Nondestructive Evaluation of Hardwood Logs: CT Scanning, Machine Vision and Data Utilization", Nondestructive Testing Evaluation, vol. No. 15, pp. 279-309, 1999.
(Continued)

*Primary Examiner* — Hoon Song
(74) *Attorney, Agent, or Firm* — GE Global Patent Operation

(57) ABSTRACT

An apparatus for materials testing of test objects using X-rays, the apparatus comprising an X-ray device, comprising: an X-ray source for irradiating a test object held in a test position; an X-ray linear diode array detector comprising at least two detection sections and configured to acquire a complete radial cross-section of the test object; and an electronic control device configured to control the X-ray device, wherein during X-ray testing the test object and the X-ray device are rotatable relative to each other only around an essentially vertical axis of rotation.

19 Claims, 7 Drawing Sheets

(52) U.S. Cl.
CPC ... *G01N 2223/309* (2013.01); *G01N 2223/321* (2013.01); *G01N 2223/3303* (2013.01); *G01N 2223/3306* (2013.01); *G01N 2223/3307* (2013.01); *G01N 2223/5015* (2013.01); *G01N 2223/627* (2013.01); *G01N 2223/643* (2013.01); *G01N 2223/645* (2013.01); *G01N 2223/646* (2013.01)

(56) References Cited

U.S. PATENT DOCUMENTS

| | | | |
|---|---|---|---|
| 4,802,195 | A | 1/1989 | Wojcienchowski et al. |
| 6,327,333 | B1 * | 12/2001 | Uchida et al. .............. 378/61 |
| 2003/0031293 | A1 * | 2/2003 | Aust et al. ................. 378/57 |
| 2004/0109532 | A1 * | 6/2004 | Ford et al. ................. 378/57 |
| 2007/0025498 | A1 * | 2/2007 | Matsuda ..................... 378/9 |
| 2009/0067575 | A1 * | 3/2009 | Seppi et al. ............... 378/57 |

FOREIGN PATENT DOCUMENTS

| | | |
|---|---|---|
| DE | 19944314 A1 | 4/2001 |
| DE | 20208174 U1 | 11/2002 |
| DE | 10163846 A1 | 7/2003 |
| DE | 10260883 B3 | 7/2004 |
| DE | 10153379 B4 | 5/2008 |
| EP | 0208250 A2 | 1/1987 |
| GB | 1420527 A | 1/1976 |
| WO | 03038419 A1 | 5/2003 |

OTHER PUBLICATIONS

PCT Search Report and Written Opinion issued in connection with corresponding Application No. PCT/EP2009/000152 on Jun. 30, 2009.

Notice of Reexamination issued in connection with corresponding CN Application No. 200880131251.6 on Jul. 10, 2013.

International Search Report and Written Opinion issued in connection with related PCT Application No. PCT/EP2008/008072 dated Jun. 17, 2009.

\* cited by examiner

US 9,341,546 B2

APPARATUS FOR MATERIALS TESTING OF TEST OBJECTS USING X-RAYS

CROSS-REFERENCE TO RELATED APPLICATIONS

This is a national stage application under 35 U.S.C. §371 (c) of prior-filed, co-pending PCT patent application serial number PCT/EP2009/000152, filed on Jan. 13, 2009 which is hereby incorporated by reference in its entirety.

BACKGROUND OF THE INVENTION

1. Field of the Invention

The field of invention relates to an apparatus for materials testing of test objects using X-rays.

2. Description of Related Art

A known apparatus to test wheels comprises an X-ray system with an X-ray tube and an image intensifier, which are both mounted on a C-arm that is pivotable around a horizontal axis. A wheel that is to be tested is conveyed by a roller conveyor to a horizontally movable carrier, which has two roller-equipped grapplers, and is moved into the test position. In the test position, an X-ray scan is taken of the wheel, for each of several swivel positions of the C-arm, as the wheel is rotated around its axis by actuating the roller-equipped grapplers which act on the lower rim flange of the wheel, and is shifted horizontally by the carrier. Thus, this is a triaxial testing device. After the X-ray test, the wheel is removed from the carrier and transferred to a roller conveyor on the output side. Afterwards, the carrier is then returned to the input side, in order to receive the next wheel to be tested.

In the multi-axial wheel test installation known from DE 101 53 379 B4, the X-ray device is stationary, but the wheel is pivotable around a transverse axis that lies in the transport plane and is rotated around its axis by actuation of roller-equipped grapplers acting on the lower rim flange. In order to allow the wheel to pivot around the transverse axis, transport chains are pivot-mounted for conveying and loading the wheel to be tested onto the swivel arms, but are pivoted away during the X-ray testing. This design is extraordinarily complicated.

DE 202 08 174 U1 discloses a triaxial X-ray test installation with a rotatable carousel carrier for conveying and loading the test objects into or out of a test position, in which the wheel to be tested is rotated around its own axis by profile wheels. The X-ray device is mounted to a C-arm that can be rotated around two horizontal axes perpendicular to each other, which is very expensive to construct. The carousel carrier is extraordinarily space-consuming in comparison to translational conveying devices.

A uniaxial wheel testing device is known with a LDA (linear diode-array)-line detector. For the X-ray test of a wheel, the wheel is transported by a chain conveyor to the X-ray device and lifted into test position from the transport plane by a gripping device and rotated there around its axis by a rotating mechanism provided on the gripping device. Pivoting the X-ray device or the wheel horizontally is not required, whereby the cost can be reduced compared to the aforementioned test devices. Due to differences in wall thickness of the test objects, it is difficult to obtain satisfactory image quality for all areas of the test object.

BRIEF DESCRIPTION SUMMARY OF THE INVENTION

The object of the embodiments of the invention is to provide a simply designed test apparatus, which achieves a high image quality in all areas of the test object at a high throughput rate.

The embodiments of the invention achieve this objective with the features of claim 1. According to embodiments of the present invention, there is provided a uniaxial testing apparatus, wherein a complete X-ray image of a test object is obtained through only the rotation of the test object relative to the X-ray device around an essentially vertical axis of rotation. Further rotations or translational movements of the test object relative to the X-ray device are not required during the testing, whereby the cost can be correspondingly reduced.

According to an exemplary embodiment there is an apparatus for materials testing of test objects using X-rays, the apparatus comprising: an X-ray device comprising an X-ray source for irradiation of a test object held in a test position; an X-ray linear diode array detector comprising at least two detection sections and configured to acquire a complete radial cross-section of the test object; and an electronic control device configured to control the X-ray device, wherein during X-ray testing, the test object and the X-ray device are rotatable relative to each other only around an essentially vertical axis of rotation.

According to embodiments of the present invention, the X-ray detector has at least two detection sections, which are each equipped to acquire a complete radial cross-section of the test object. A radial cross-section is a cross-section extending radially outward from an axis of rotation; in particular, a full cross-section includes two radial cross-sections running through the axis of rotation. This enables it, for example, in the case of two detection sections with a complete rotation of 360°, to acquire two complete individual images of the test object, so that the image quality can be greater in comparison to the quality of only an individual image. In particular, each individual image is preferably taken with different operating parameters for the X-ray device, for example, an individual image can be taken with operating parameters adjusted for the thick-walled areas of the test object and an individual image can be taken with operating parameters adjusted for the thin-walled areas of the test object. In this way, X-ray images of high quality are obtained both of the thick-walled areas and the thin-walled areas. Also, detection sections can be provided acquiring more than two complete radial cross-sections of the test object, in order to obtain in a complete rotation of 360° more than two complete individual images of the test object or alternatively with a rotation of less than 360° two complete individual images of the test object. Amplification factors for the X-ray detector come into consideration as operating parameters that can be adjusted. Preferably, therefore, the at least two detection sections are independently controllable, particularly through applying different amplification factors. Also, for example, different X-ray energies and/or outputs are possible for the X-ray tubes.

In an especially preferred embodiment, each individual image is taken with a rotation angle of less than 360°, in particular, approximately 180°.

The embodiments of the invention are preferably used for the testing of essentially rotationally symmetrical objects, which through the rotation of 360°/n with n=2 or 3, the images merge into themselves. An especially preferable use relates to the testing of cast aluminum wheels for automobiles. Other conceivable uses relate, for example, to automobile tires or brake discs. However, the embodiments of the invention are also applicable to the testing of non-rotationally symmetrical parts, for example, chassis parts.

DETAILED DESCRIPTION OF THE INVENTION

Figure 1:
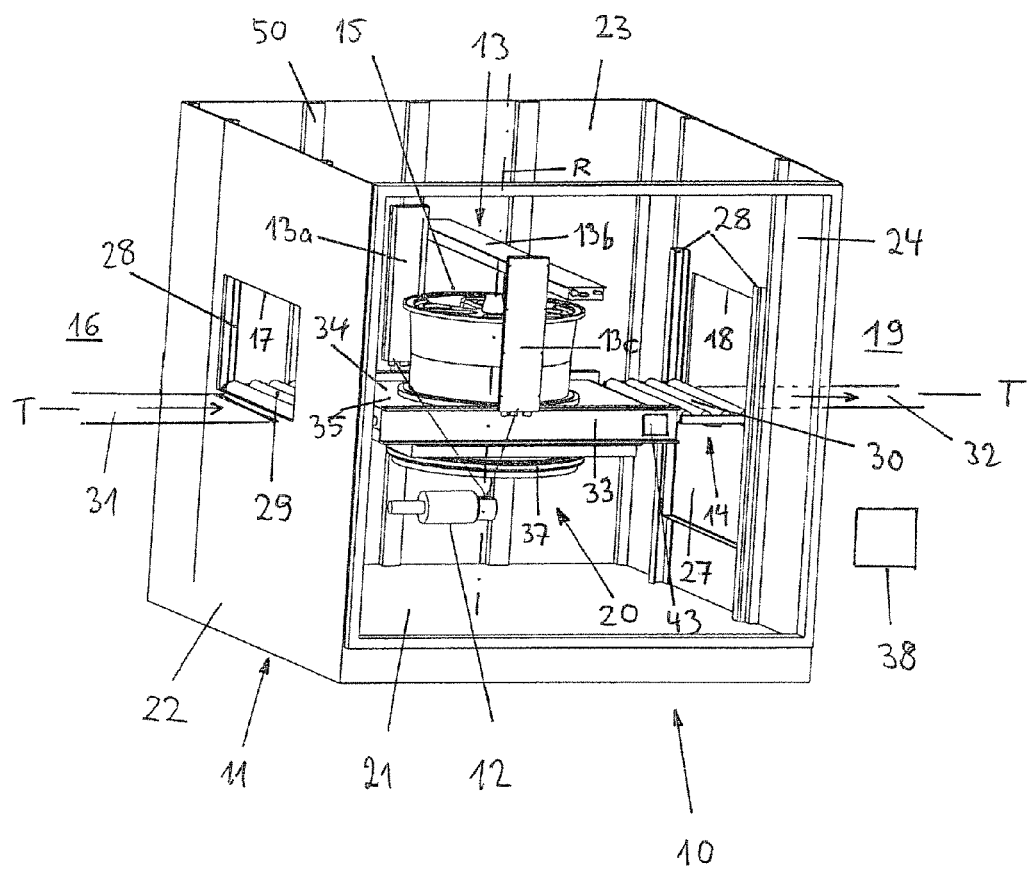
FIG. 1 shows a perspective view of a test apparatus in a loading state.

The test apparatus 10 comprises a radiation protection chamber 11 and an X-ray device 20 disposed in the radiation protection chamber 11, wherein the X-ray device 20 has an X-ray source 12 for irradiation of a test object 15, disposed on a carrier 33, and an X-ray detector 13 for recording the radiation passing through the test object 15. The radiation protection chamber 11 completely shields the environment during operation from the X-rays generated by the X-ray source 12 and for that purpose includes side-walls 22 to 25, a top wall 49 and, if necessary, a bottom wall 21, which are built, for example, from plates with a lead layer and support rods 50. The top wall 49 and the side wall 25 are left out in FIGS. 1 and 8 for a better visibility.

A side-wall 22 on the input side has an input opening 17 for test objects 15 to enter. An opposite side-wall 24 on the output side has an output opening 18 for test objects 15 to exit. The radiation protection chamber 11 has sliders 26, 27 guided by guide rails 28 with rollers 51 for closing the input opening 17 and the output opening 18 during testing and for opening them in the loading operation. One of the side-walls 22 to 25 can preferably have a door (not shown), in order to permit access to the chamber by service personnel.

Figure 2:
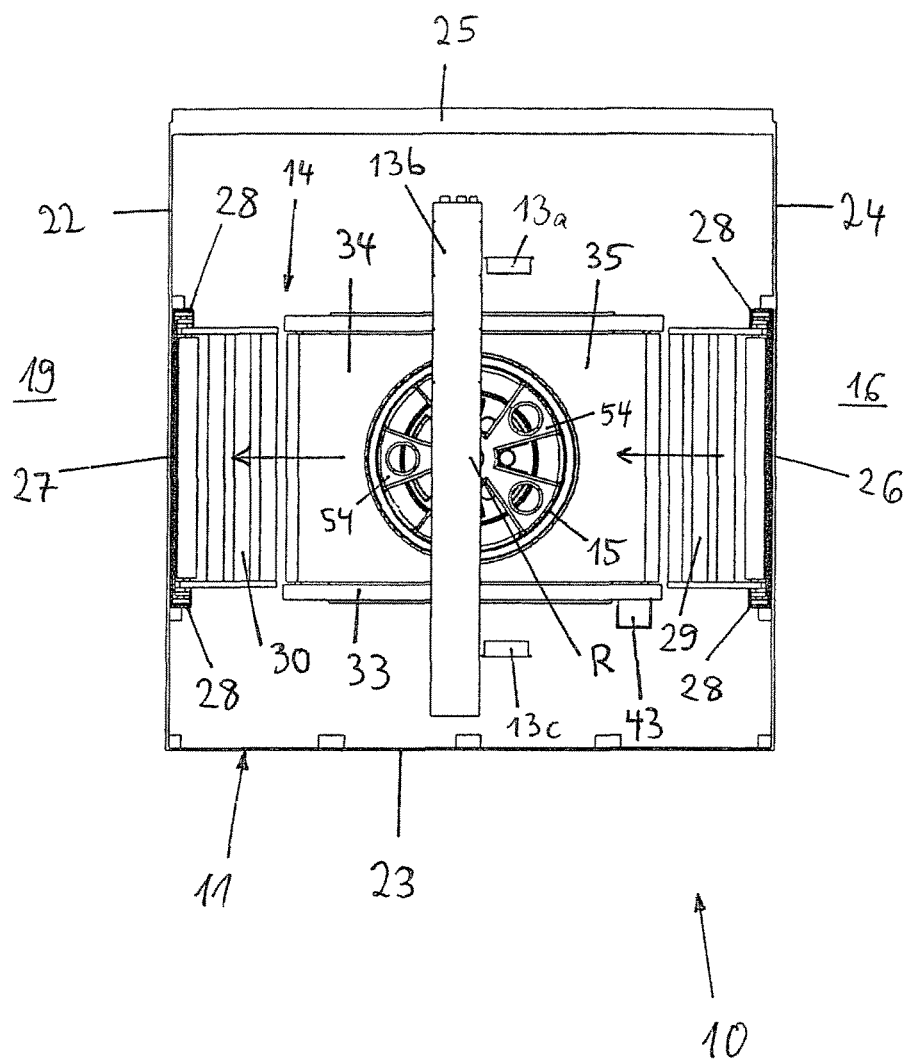
FIG. 2 shows a top view of the test apparatus from FIG. 1.
Figure 6:
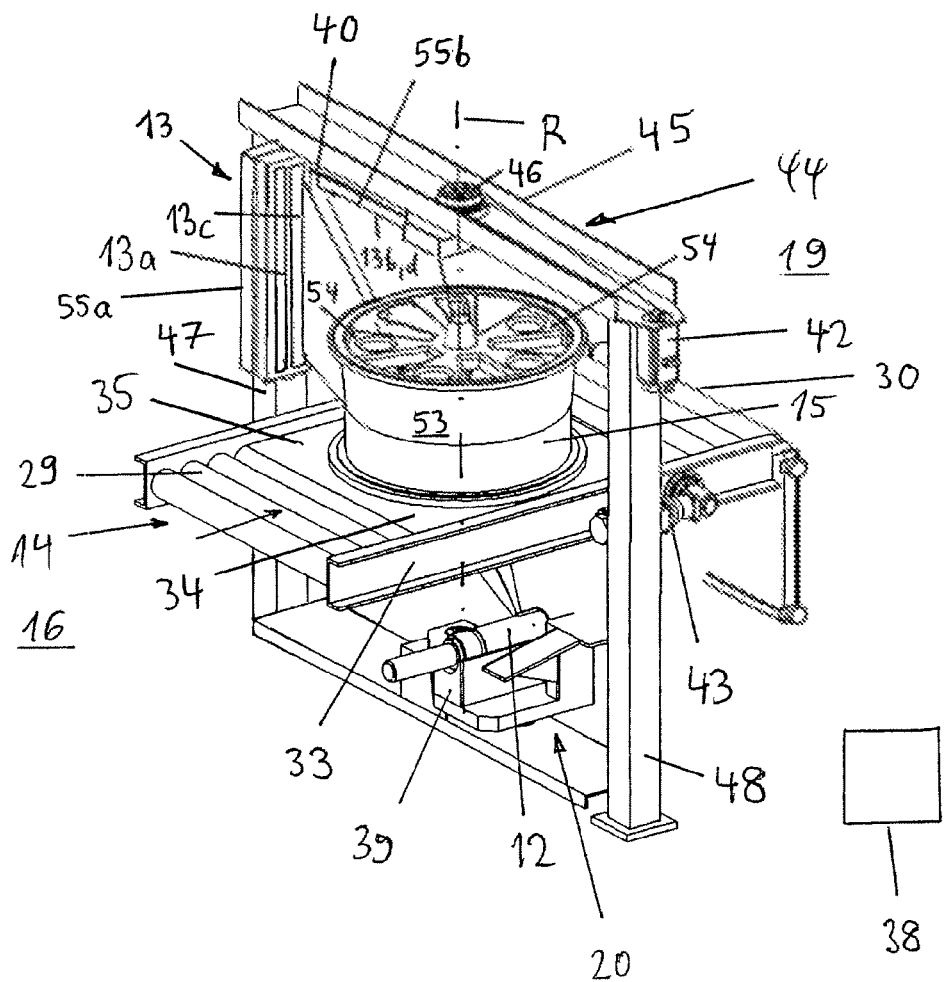
FIG. 6 shows a cut-away perspective of a test apparatus in a further embodiment.

Furthermore, the test apparatus 10 includes a translational conveyor 14 for the serial conveyance of test objects 15 through the radiation protection chamber 11 in a transport direction, such as indicated, for example, in FIGS. 1, 2 and 6 by the arrows. The conveyor 14 comprises a loading device 29 disposed in the interior of the radiation protection chamber 11 for the conveyance of the test objects to the carrier 33, an unloading device 30 disposed in the interior of the radiation protection chamber 11 for discharging the test objects from the carrier 33 and, if necessary, corresponding external conveyors 31, 32 on the input side 16 and the output side 19. The loading device 29 and the unloading device 30 are designed, for example, as roller conveyors, wherein the rollers can be actively actuated for a precise transfer to or from the carrier 33. The loading device 29 is attached to the slider 26, and the unloading device 30 to the slider 27, so that a shift of the sliders 26, 27 into the open position at the same time shifts the loading device 29 and the unloading device 30 into the transport plane, and a shift of the sliders 26, 27 into the closed position at the same time shifts the conveying devices 29, 20 out of the transport plane.

Figure 3:
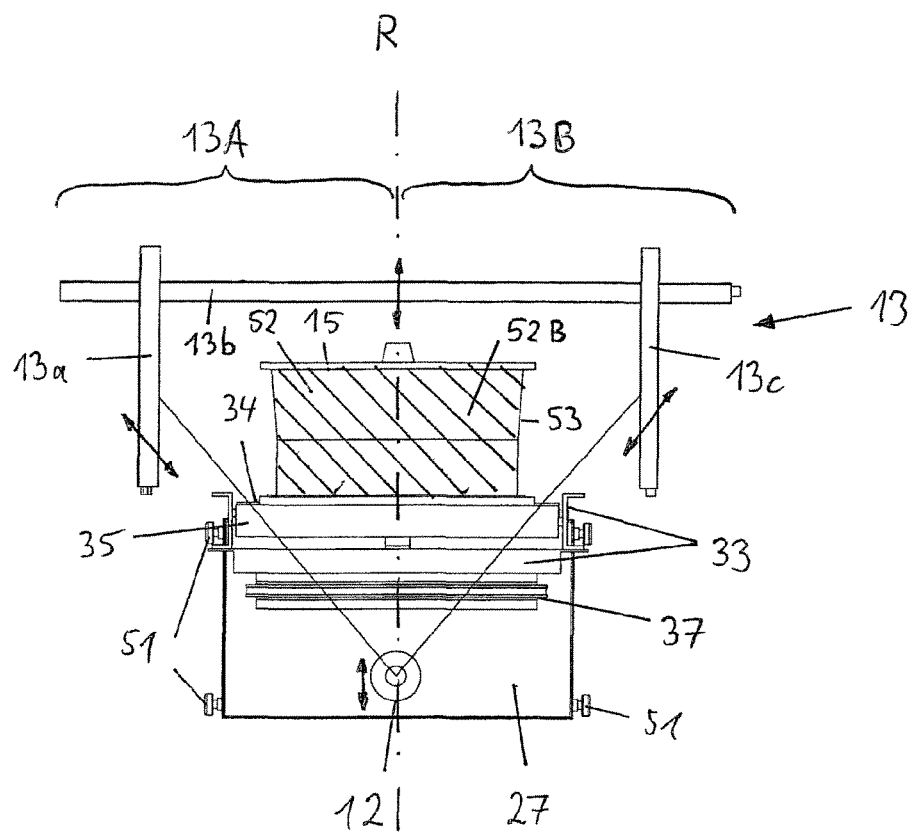
FIG. 3 shows a view of the test apparatus from FIG. 1 from the transport direction.

In the embodiments according to FIGS. 1 to 3 and 8, the X-ray tube 12 is a fan beam-X-ray tube with a fan angle of at least 45°, preferably at least 60°, more preferably at least 75°, for example, approximately 90°, so that with suitable arrangement of the X-ray tube 12, normal automobile wheels can be X-rayed through their entire cross-section, see particularly FIG. 3. In this embodiment the central X-ray beam from the X-ray source 12 lies on the axis of rotation R.

The X-ray detector 13 is a linear diode-array (LDA) detector which is line-shaped or composed of line-shaped sections and is suitably dimensioned and disposed in order to record the entire X-ray beam. The X-ray detector 13 is preferably curved, particularly C-, U- or L-shaped, arranged around the test object, so that at a given detection angle the length of the detector can be substantially reduced compared to an individual detector row. The X-ray detector 13 consists of several detector elements 13a, 13b, 13c arranged at an angle to each other. In the illustrative embodiment according to FIGS. 1 to 3, the U-shaped X-ray detector 13 includes, for example, three detector rows 13a, 13b, 13c with a horizontal detector row 13b and two vertical detector rows 13a, 13c. The X-ray detector 13 is arranged approximately symmetrically around the axis of rotation R.

As is obvious from FIG. 3, the X-ray detector 13 is preferably sufficiently dimensioned and suitably arranged, in order to acquire two complete radial cross-sections 52A of the test object 15—in FIG. 3 to the right of the axis of rotation R. The detector 13, therefore, can be dissected into a detection section 13A for the acquisition of the complete radial cross-section 52A and into a detection section 13B for the acquisition of the complete radial cross-section 52B, wherein in this example the median detector row 13b is dedicated in each case in equal shares to both detector sections 13A, 13B.

In order to permit an adjustment of the test objects 15 of different dimensions, the X-ray source 12 and/or the X-ray detector 13 or the detector elements 13a, 13b, 13c are preferably movable relative to each other, particularly in a plane perpendicular to the transport direction, as indicated in FIG. 3 with double arrows. In particular, the horizontal detector element 13b can be displaced vertically or with a vertical component; and/or the vertical detector elements 13a, 13c horizontally or with a horizontal component. The adjustment of the position of the X-ray source 12 and the X-ray detector 13 occurs for each test object 15 once before the activation of the X-ray tube 12; during the X-ray test, no shift of the X-ray source 12 or of the X-ray detector 13 takes place.

The carrier 33 has an essentially plane bearing surface 34, on which the test object 15 rests only during the transport and the entire X-ray test, without having to be held by gripping devices or the like. The bearing surface 34 is formed in particular from the upper surface of a continuously revolving conveying mechanism, here of a transport belt 35. The transport belt 35 is activated by a drive 43 in order to transport a test object 15 from the conveying device 29 into the test position and a test object 15 once tested, to the unloading device 30. The carrier 33 is therefore designed as a translational conveyor and part of the continuous conveyor 14. The transport belt 35 is essentially X-ray transparent; generally this is applicable to the carrier 33 at least in the irradiated area.

For carrying out the X-ray testing of a test object 15, the carrier 33, along with the test object resting on it, is rotatable overall around a vertical axis of rotation R by a rotational bearing 37 and a drive 36. Beforehand, the sliders 26, 27 for closing the chamber openings 17, 18 are shifted, whereby at the same time the conveyors 29, 39 attached thereto are shifted from the transport plane upwards, so that they do not impede the rotation of the carrier 33. The conveying mechanism 35 is brought to a stop when the test object is in the test position, which can be detected by a sensor (not shown). In the process, it is not necessary that a possible axis of rotation of the test object 15 coincides with the axis of rotation R of the carrier 33. Devices for centering the test object 15 around the axis of rotation R can also be provided, for example, lateral sliders for horizontally shifting the carrier 33.

If the test object 15 is in the test position, the X-ray source 12 is on and only the carrier 33 rotates around the vertical axis of rotation. The X-ray tube 12 supplies normal X-ray radiation for the materials being tested with at least 60 kV, preferably at least 100 kV and/or at least 1 kW, preferably at least 3 kW. The entire X-ray testing of a test object 15 occurs only through rotation around the vertical axis of rotation R; any further pivoting or shifting of the test object 15 and/or the X-ray device 20 is not required for this purpose. Mechanisms acting on the test object 15, in order to set the test object 15 into rotation, for example, tapered rollers or carriers, are unnecessary. The test object 15 remains in the transport plane T during the entire procedure, including the X-ray testing, so that an intricate and time-consuming removal of the test object from the conveyor 14 or from the transport plane T is eliminated.

Due to the acquisition of two complete radial cross-sections 52A, 52B of the test object 15 through the detection sections 13A, 13B, a rotation of 180° is sufficient in the embodiment according to FIGS. 1 to 3, in order to acquire a complete individual image of the test object 15. In comparison to a conventional test device, in which a rotation of 360° is required to acquire a complete individual image, the test duration can thus be significantly reduced.

In many cases, the test object 15 has areas of different wall thickness. For example, in the case of an automobile wheel, the rim well 53 is relatively thin-walled and the spokes 54 are relatively thick-walled. Preferably, in these cases, many complete individual images of the test object are acquired, wherein each individual image is acquired with a set of parameters for the X-ray device adjusted to the wall thickness. For example, in the case of an automobile wheel, a complete individual image is acquired with a set of parameters for the X-ray device adjusted to the rim well and a complete individual image with a set of parameters for the X-ray device adjusted to the spokes, in each case through the rotation of 180°. The acquired individual images are subsequently combined in the control device 38 into an overall picture, particularly where they are suitably weighted, and then interposed on one another. The generated overall picture of the test object 15 can be displayed for a user on a display terminal.

The acquisition of multiple individual images can occur in the embodiment according to FIGS. 1 to 3, particularly because the entire X-ray detector 13 is operated with a uniform set of parameters adjusted to the rim well and is rotated over 180°, and is subsequently operated with a uniform set of parameters adjusted to the spokes and is rotated over 180°, or vice versa. Alternatively to this, the detection section 13A can also, for example, be operated with a set of parameters adjusted to the rim well and the detection section 13B with a set of parameters adjusted to the spokes and operated over 360°, or vice versa. In each case, two complete individual images can be acquired through rotation of over 360°.

After recording the X-ray image or the X-ray images, the X-ray source 12 is turned off. The rotation of the carrier 33 is terminated in a position suitable for unloading. The sliders 26, 27 are shifted into the open position, whereby the loading device 29 and unloading device 30 are shifted into the transport plane T. The transport belt 35 of the carrier 33, the unloading device 30 for the removal of the test object 15 through the output opening 18, and the loading device 29 for the loading of the next test object are all actuated after the test object has been tested.

All aforementioned procedures are automatically controlled by an electronically programmed control device 38, which is connected for this purpose, for example, via a data bus with the corresponding drives, sensors, actuators and the X-ray device 20. The control device 38 can also be programmed for evaluation of the X-ray data recorded by the X-ray detector 13 and can be connected with an input/output terminal, which is not shown, for the operation of the test apparatus 10 and for the display of the test results.

Figure 4:
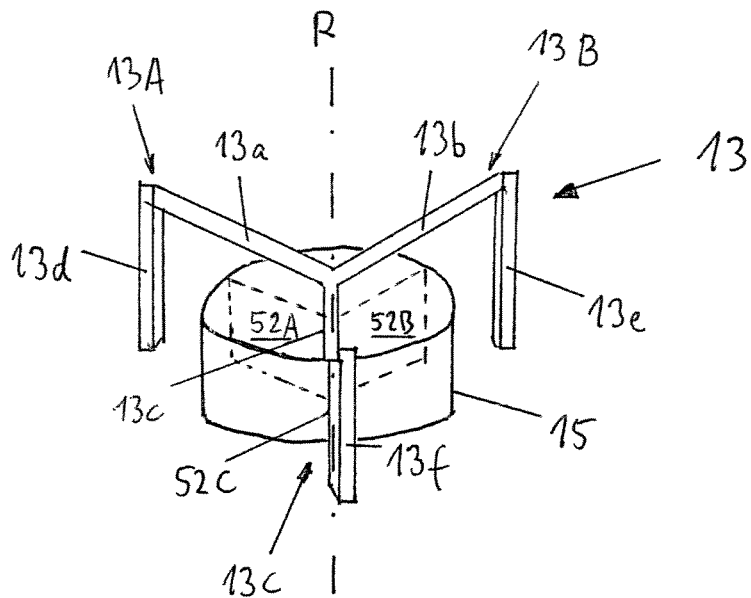
FIG. 4 shows a schematic perspective view of a detector arrangement in another embodiment.

The embodiment according to FIG. 4 makes clear that the X-ray detector 13 can be equipped for the acquisition of more than two, in this case of three radial cross-sections 52A, 52B, 52C. The X-ray detector 13 comprises six detector rows 13a to 13f. The detector rows 13a, 13b, 13c are arranged horizontally in the form of a star with equal angular distances of 120° in each case. At the open end of each horizontal detector row 13a, 13b, 13c, a vertical detector row 13d, 13e, 13f is attached. The detector rows 13a and 13d form a first detection section 13A for the acquisition of a first radial cross-section 52A, the detector rows 13b and 13e form a second detection section 13B for the acquisition of a second radial cross-section 52B, and the detector rows 13c and 13f form a third detection section 1C for the acquisition of a third radial cross-section 52C of the test object 15. If all detection sections 13A to 13C are operated with the same amplification factors, a complete individual image of the test object 15 can be obtained through rotation at only 120°. If in each case the detection sections 13A to 1C are operated with different amplification factors, three complete individual images of the test object can be obtained through the rotation of 360°.

Figure 5:
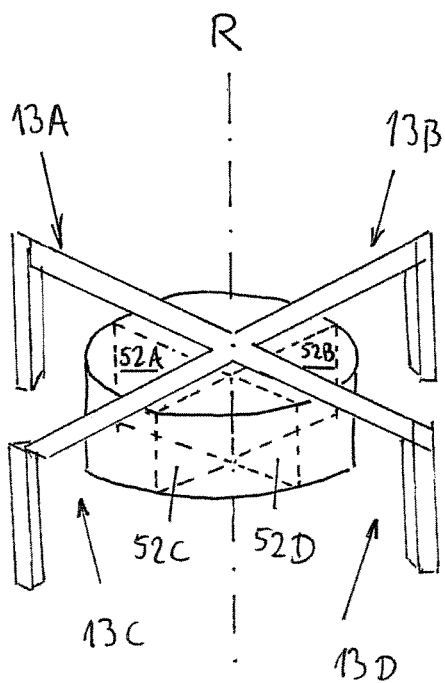
FIG. 5 shows a schematic perspective view of a detector arrangement in a further embodiment.

The embodiment according to FIG. 5 is designed like the embodiment according to FIG. 4, wherein four detection sections 13A to 13D with angular distances of 90° are provided for the acquisition of four radial cross-sections 52A to 52D. In this embodiment, preferably two fan beam-X-ray tubes, which are not shown, are provided, wherein an X-ray tube is provided for illumination of the detection sections 13A and 13D and an X-ray tube for illumination of the detection sections 13B and 13C. For the testing of automobile wheels, the detection sections 13A and 13D, for example, can be operated with amplification factors adjusted to the rim well and the detection sections 1B and 13C with amplification factors adjusted to the spokes, or vice versa. Two complete individual images of the test object 15 can then be obtained through rotation of only 180°. If all of the detection sections 13A to 13D are operated with the same amplification factors, a complete individual image of the test object 15 can be obtained through rotation at only 90°. If the detection sections 13A to 13D are operated with different amplification factors in each case, four complete individual images of the test object 15 can be obtained through the rotation of 360°.

Figure 7:
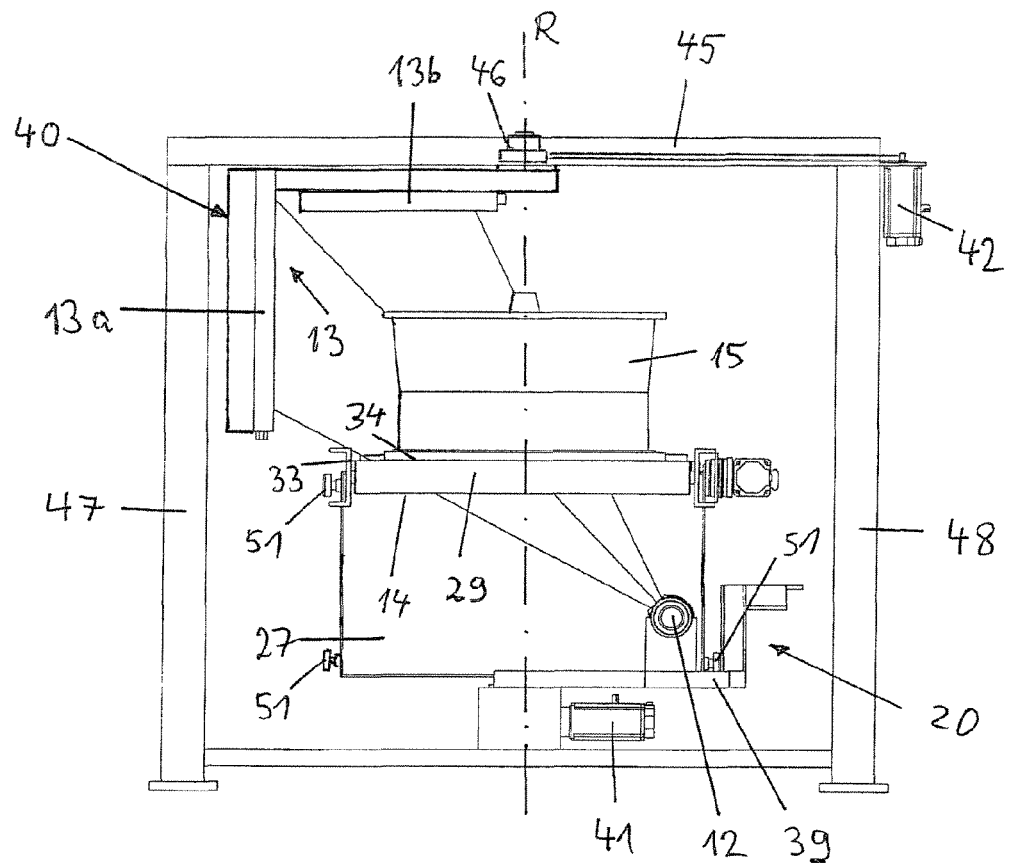
FIG. 7 shows a view of the test apparatus from FIG. 6 from the transport direction.

FIGS. 6 and 7 show an alternative embodiment, in which the carrier 33 is stationary during the X-ray testing and therefore has no swivel 37, and instead the entire X-ray device 20 rotates uniformly around the vertical axis of rotation R. For the sake of clarity, the chamber 11 is not shown in FIGS. 6 and 7. The X-ray tube 12 and the X-ray detector 13 are preferably installed on a carrier 39 or 40 which are rotatable around the vertical axis of rotation R, and are arranged above or below the transport plane and each have their own rotary drive 41 or 42, whereby a complete rotation is possible without a collision with the conveyor 14. The rotary drives 41, 42 are controlled by the electronic control device 38, so that a synchronous rotation of the X-ray source 12 and the X-ray detector 13 is ensured. The rotation carriers 39 and 40 are therefore preferably decoupled mechanically and coupled only through a drive control. However, this is not necessarily the case—a mechanical coupling of the rotation carriers 39 and 40 is also conceivable. The test device 10 comprises a carrier frame 44 for the rotational bearing 46 for the rotatable carrier 40 disposed above the transport plane. The carrier frame 44 can comprise, in particular, a horizontal carrier 45 and vertical carriers 47, 48. Because the carrier 33 is stationary, the loading device 29 and the unloading device 30 do not have to be vertically displaceable and can, for example, be installed on the carrier 33.

In the embodiment according to FIGS. 6 and 7, the central X-ray beam from the X-ray source 12 has an angle in the range of 30° to 60° with the axis of rotation R, so that the half cross-section of the test object 15 is illuminated, as is most evident from FIG. 7. The X-ray detector 13 is arranged asymmetrically to the axis of rotation R. In this embodiment, a conventional X-ray tube, which has a fan beam of maximally 40°, and an overall L-shaped X-ray detector 13 provided with a vertical double line 55a and a horizontal double line 55b. The double line 55a has two parallel, independently controllable detector rows 13a, 13c, and the double line 55b has two parallel independently controllable detector rows 13b, 13d. The detector rows 13a and 13b form a first detection section for the acquisition of a first complete radial cross-section of the test component 15, and the detector rows 13b and 13d form a second detection section for the acquisition of a second complete radial cross-section of the test component 15. Through the activation of the first detection section 13a and 13b, with amplification factors adjusted to the rim well, and the activation of the second detection section 13c and 13d with amplification factors adjusted to the spokes 54, or vice versa, two corresponding complete individual images of the automobile wheel 15 can be acquired through rotation of the X-ray device 20 through 360°.

In an embodiment that is not shown, analogous to FIGS. 6 and 7, the X-ray device 20 with L-shaped X-ray detector 13 is fixed and the test component 15 is rotatable for the X-ray testing.

Figure 8:
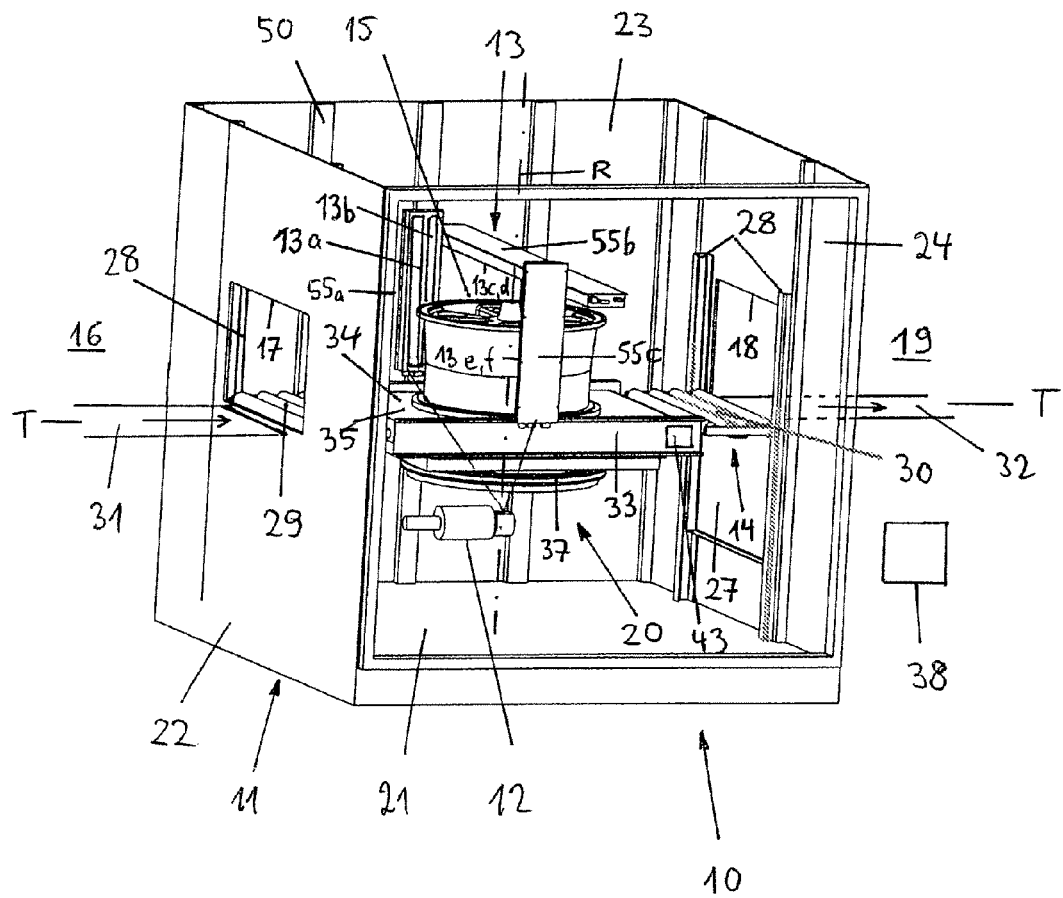
FIG. 8 shows a perspective view of the test apparatus in the loading state in a further embodiment.

The embodiment according to FIG. 8 differs from that according to FIGS. 1 to 3 in that the X-ray detector 13 has three double lines 55a, 55b, 55c, wherein each double line 55a, 55b, 55c has two parallel, independently controllable detector rows 13a, 13b or 13c, 13d or 13e, 13f. The detector rows 13a, 13c, and 13f form a first U-shaped detection section for the acquisition of a first complete cross-section of the test object 15, and the detector rows 13b, 13d, and 13f form a second detection section for the acquisition of a second complete cross-section of the test object 15. Through activation of the first detection section 13a, 13c, 13e, with amplification factors adjusted to the rim well, and activation of the second detection section 1c, 13d, 13f with amplification factors adjusted to the spokes 54, or vice versa, two corresponding complete individual images of the automobile wheel 15 can be acquired through rotation, here of the test component 15, at only 180°.

In the embodiments according to FIGS. 6 to 8, more than two independently controllable detection surfaces arranged in parallel can also be provided per detector row 55a, 55b.

What is claimed is:

1. An apparatus for materials testing of a test object using X-rays, the apparatus comprising:
   a carrier having a first surface and a second surface;
   an X-ray device comprising an X-ray source for irradiation of the test object held in a test position on the first surface of the carrier;
   an X-ray linear diode array detector comprising at least two detection sections and configured to acquire a complete radial cross-section of the test object, the detection sections arranged at an angle to each other, at least a first detection section arranged to face a horizontal surface of the test object and at least a second detection section arranged to face a vertical surface of the test object; and
   an electronic control device configured to control the X-ray device,
   wherein during X-ray testing to acquire a complete overall cross-section of the test object, the carrier is configured to rotate relative to the X-ray device and the X-ray linear diode array detector only around a vertical axis of rotation while the X-ray device and the X-ray linear diode array detector remain stationary, the carrier to rotate while acquisition of the overall cross-section of the test object is actively occurring.

2. The apparatus according to claim 1, wherein the X-ray detector is arranged in a C-, U-, or L-shape around the test object.

3. The apparatus according to claim 1, wherein the at least two detection sections are L-shaped.

4. The apparatus according to claim 1, wherein the control device activates the X-ray device for acquisition of at least two complete individual images of the test object, wherein different sets of parameters for the X-ray device are used for each image.

5. The apparatus according to claim 4, wherein for the acquisition of an individual image, the test object and the X-ray device are rotated relative to each other at a rotation angle of less than 360°.

6. The apparatus according to claim 4, wherein for the acquisition of an individual image, the test object and the X-ray device are rotated relative to each other at a rotation angle of approximately 180°.

7. The apparatus according to claim 4, wherein the control device is configured to combine the at least two complete individual images into an overall picture.

8. The apparatus according to claim 4, wherein the control device is configured to adjust the operating parameters for different thick-walled areas of the test object.

9. The apparatus according to claim 1, further comprising a carrier, wherein the carrier, together with the test object held on it, are rotatable around the axis of rotation.

10. The apparatus according to claim 1, wherein the test object remains in a continuous transport plane while it is loaded into the apparatus for materials testing and during X-ray testing.

11. The apparatus according to claim 1, wherein the X-ray source is a beam-X-ray tube with a fan angle of at least 45°.

12. The apparatus according to claim 1, wherein the X-ray source and/or the X-ray detector are displaceable relative to the test object being tested in order to adapt to different test objects.

13. The apparatus according to claim 1, wherein the control device is configured to automatically load and unload the test object into or out of the test position.

14. The apparatus according to claim 1, further comprising a radiation protection chamber shielding the environment outside of the radiation protection chamber from X-rays.

15. The apparatus according to claim 1, wherein one of the at least two detection sections extends parallel to the vertical axis of rotation and the other of the at least two detection sections extends perpendicular to the vertical axis of rotation.

16. The apparatus according to claim 1, wherein the X-ray source is configured to face the second surface of the carrier and at least a portion of the X-ray linear diode array detector is configured to face the first surface of the carrier.

17. An apparatus for materials testing, of a test object using X-rays, the apparatus comprising:
   a carrier having a first surface and a second surface;
   an X-ray device comprising an X-ray source for irradiation of the test object held in a test position on the first surface of the carrier;
   an X-ray linear diode array detector comprising at least two detection sections and configured to acquire a complete radial cross-section of the test object, the detection sections arranged at an angle to each other, at least a first detection section arranged to face a horizontal surface of the test object and at least a second detection section arranged to face a vertical surface of the test object; and
an electronic control device configured to control the X-ray device,
wherein during X-ray testing to acquire a complete overall cross-section of the test object, the X-ray device and the X-ray linear diode array detector are configured to rotate relative to the carrier only around a vertical axis of rotation while the carrier remains stationary.

18. The apparatus according to claim 17, wherein one of the at least two detection sections extends parallel to the vertical axis of rotation and the other of the at least two detection sections extends perpendicular to the vertical axis of rotation.

19. The apparatus according to claim 17, wherein the X-ray source is configured to face the second surface of the carrier and at least a portion of the X-ray linear diode array detector is configured to face the first surface of the carrier.

\* \* \* \* \*